US012059583B2

United States Patent
Xu et al.

(10) Patent No.: US 12,059,583 B2
(45) Date of Patent: *Aug. 13, 2024

(54) ULTRASONIC TRANSDUCER AND FOCUSED ULTRASOUND TREATMENT DEVICE

(71) Applicant: CHONGQING HAIFU MEDICAL TECHNOLOGY CO., LTD., Chongqing (CN)

(72) Inventors: Guihua Xu, Chongqing (CN); Fangwei Ye, Chongqing (CN); Guangrong Lei, Chongqing (CN); Dan Song, Chongqing (CN); Huawei Liu, Chongqing (CN); Sanyong Li, Chongqing (CN)

(73) Assignee: CHONGQING HAIFU MEDICAL TECHNOLOGY CO., LTD., Chongqing (CN)

( * ) Notice: Subject to any disclaimer, the term of this patent is extended or adjusted under 35 U.S.C. 154(b) by 1045 days.

This patent is subject to a terminal disclaimer.

(21) Appl. No.: 16/963,286

(22) PCT Filed: Sep. 7, 2018

(86) PCT No.: PCT/CN2018/104603
§ 371 (c)(1),
(2) Date: Jul. 20, 2020

(87) PCT Pub. No.: WO2019/140927
PCT Pub. Date: Jul. 25, 2019

(65) Prior Publication Data
US 2022/0331615 A1     Oct. 20, 2022

(30) Foreign Application Priority Data
Jan. 22, 2018 (CN) .......................... 201810059389.5

(51) Int. Cl.
*A61N 7/02* (2006.01)
*A61N 7/00* (2006.01)

(52) U.S. Cl.
CPC ........ *A61N 7/02* (2013.01); *A61N 2007/0065* (2013.01); *A61N 2007/0069* (2013.01)

(58) Field of Classification Search
CPC .............. A61N 7/02; A61N 2007/0065; A61N 2007/0069; A61N 2007/0043;
(Continued)

(56) References Cited

U.S. PATENT DOCUMENTS

| 5,873,845 A | 2/1999 | Cline et al. |
| 7,602,672 B2 * | 10/2009 | Lai .......................... A61N 7/02 367/138 |

(Continued)

FOREIGN PATENT DOCUMENTS

| CN | 101140354 A | 3/2008 |
| CN | 101190436 A | 6/2008 |

(Continued)

*Primary Examiner* — Alexei Bykhovski
(74) *Attorney, Agent, or Firm* — The Webb Law Firm (57) ABSTRACT

The present disclosure provides an ultrasonic transducer and a focused ultrasound treatment device. The ultrasonic transducer includes a sound generation unit and a sound emitting surface, the sound emitting surface being a spherical surface having a first notch, a second notch and a third notch, wherein one great circle of a sphere corresponding to the sound emitting surface is a main great circle, the first notch and the second notch are respectively positioned at two intersections of the spherical surface and a diameter perpendicular to the main great circle, and the third notch connects the first notch with the second notch; each cross-section of the sound emitting surface parallel to the main great circle is in a shape of an arc; and the ultrasonic wave generated by (Continued)

the sound generation unit is focused on a center of the sphere corresponding to the sound emitting surface.

19 Claims, 10 Drawing Sheets

(58) Field of Classification Search
CPC .... A61N 2007/0056; A61N 2007/0082; A61N 7/022; A61N 2007/0086; B06B 1/0637; B06B 1/0651; B06B 3/00; G10K 11/28; A61B 18/04; A61B 2018/00577
See application file for complete search history.

(56) References Cited

U.S. PATENT DOCUMENTS

| | | | |
|---|---|---|---|
| 8,040,756 B2 | 10/2011 | Wang et al. | |
| 2006/0058678 A1* | 3/2006 | Vitek | A61B 8/0808 600/459 |
| 2013/0023801 A1* | 1/2013 | Wang | B06B 1/0637 601/2 |
| 2018/0071553 A1* | 3/2018 | Vortman | A61N 7/00 |

FOREIGN PATENT DOCUMENTS

| | | |
|---|---|---|
| CN | 101740017 A | 6/2010 |
| CN | 102210910 A | 10/2011 |
| CN | 103520844 A | 1/2014 |

\* cited by examiner

XOZ plane  YOZ plane  XOY plane

ULTRASONIC TRANSDUCER AND FOCUSED ULTRASOUND TREATMENT DEVICE

CROSS-REFERENCE TO RELATED APPLICATIONS

This application is the United States national phase of International Application No. PCT/CN2018/104603 filed Sep. 7, 2018, and claims priority to Chinese Patent Application No. 201810059389.5 filed Jan. 22, 2018, the disclosures of which are hereby incorporated by reference in their entirety.

BACKGROUND OF THE INVENTION

Field of the Invention

The present disclosure belongs to the field of high intensity focused ultrasound technology, and particularly relates to an ultrasonic transducer and a focused ultrasound treatment device.

Description of Related Art

High Intensity Focused Ultrasound (HIFU) technology has been widely used in the fields of medical treatment, scientific research, material processing, and the like. Ultrasound is focused at a specific location by using the focusability and penetrability of ultrasound, and high energy in the focal region is used to treat diseases, excite reactions, and change material properties. For example, the high intensity focused ultrasound technology has been used clinically to treat benign and malignant tumors such as liver cancer, breast cancer, kidney cancer, bone tumor, uterine fibroid, etc., and the principle thereof is to focus ultrasound at a lesion in a human body, so that high energy density mechanical energy in the focal region is converted into heat energy to cause coagulative necrosis (also called ultrasound thermal ablation) of diseased tissues; meanwhile, because the ultrasonic energy density on the beam path is low, it can be guaranteed that influence on normal tissues around the diseased tissues and on the beam path is little or acceptable.

An ultrasonic transducer is a core component of the high intensity focused ultrasound technology, and is used for converting electric energy into mechanical energy and emitting ultrasound in a normal direction from all positions of a sound emitting surface so as to focus the emitted ultrasound. The sound emitting surfaces of existing focused ultrasonic transducers are mostly in the shape of a spherical cap, and the ultrasound emitted by the existing focused ultrasonic transducer is a traveling wave and is focused near the spherical center of the spherical cap. Due to the characteristics of ultrasound, the focal region of the existing ultrasound transducer actually has a shape similar to a cigar or a spindle, its length in the direction of the sound axis is relatively large and generally exceeds 10 mm, and the dimensions in the other two short axes range from 2 mm to 3 mm (taking the ultrasound frequency of 1 MHz as an example).

The existing ultrasonic transducer has a large focal region range, low energy concentration, low energy density at the focal region, and an acoustic pressure that can only reach $10^7$ Pa magnitudes at most, so it cannot ablate diseased tissues quickly, the treatment time is long and the treatment effect is poor.

In addition, a large amount of non-uniform tissues such as bones, organs containing air, fat and the like exist in a human body, and they can cause serious scattering and reflection to the ultrasound emitted by the existing ultrasonic transducer, and thus make the ultrasound propagate in a seriously nonlinear manner, which in turn causes an unpredictable deviation and distortion of the focal region, and influences the safety of the treatment.

SUMMARY OF THE INVENTION

The present disclosure at least partially solves the problems of large size and cigar-like shape of the focal region of the existing ultrasonic transducer, and provides an ultrasonic transducer and a focused ultrasound treatment device which can form a spherical focal region having a small size.

As a technical solution adopted to solve the technical problem of the present disclosure, there is provided an ultrasonic transducer, including a sound generation unit and a sound emitting surface, wherein the sound generation unit is configured to generate an ultrasonic wave, and the sound emitting surface is a spherical surface having a first notch, a second notch and a third notch, wherein one great circle of a sphere corresponding to the sound emitting surface is a main great circle, the first notch and the second notch are respectively positioned at two intersections of the spherical surface and a diameter perpendicular to the main great circle, and the third notch connects the first notch with the second notch;

within certain distances from the main great circle respectively at both sides of the main great circle, a cross-section of the sound emitting surface parallel to the main great circle is in a shape of an arc, an opening of the arc corresponds to the third notch, and a central angle corresponding to the arc is larger than 180 degrees and smaller than 360 degrees; and the sound emitting surface is capable of reflecting ultrasound, and the ultrasonic wave generated by the sound generation unit is focused on a center of the sphere corresponding to the sound emitting surface.

Optionally, an edge of the first notch and an edge of the second notch are in a first plane and a second plane, respectively.

Optionally, the first plane and the second plane are both parallel to the main great circle.

Optionally, a distance between the first plane and the second plane is in a range of 80 mm to 1000 mm.

Optionally, the distance between the first plane and the second plane is in a range of 150 mm to 500 mm.

Optionally, a distance between the first plane and the main great circle is equal to a distance between the second plane and the main great circle.

Optionally, each cross-section of the sound emitting surface parallel to the main great circle is in a shape of an arc, and the central angle corresponding to the arc is larger than 180 degrees and smaller than 360 degrees.

Optionally, an opening of the arc in each cross-section of the sound emitting surface parallel to the main great circle is oriented in a same direction.

Optionally, central angles corresponding to the arcs in all cross-sections of the sound emitting surface parallel to the main great circle are equal.

Optionally, within certain distances from the main great circle respectively at both sides of the main great circle, the central angle corresponding to the arc in the cross-section of the sound emitting surface parallel to the main great circle is larger than 180 degrees and smaller than 300 degrees.

Optionally, within certain distances from the main great circle respectively at both sides of the main great circle, the central angle corresponding to the arc in the cross-section of the sound emitting surface parallel to the main great circle is larger than 200 degrees and smaller than 280 degrees.

Optionally, the certain distances from the main great circle respectively at both sides of the main great circle are each in a range of 40 mm to 500 mm.

Optionally, a diameter of the sphere corresponding to the sound emitting surface is in a range of 100 mm to 3000 mm.

Optionally, the diameter of the sphere corresponding to the sound emitting surface is in a range of 200 mm to 2000 mm.

Optionally, the sound emitting surface is symmetric with respect to the main great circle.

As a technical solution adopted to solve the technical problem of the present disclosure, there is provided a focused ultrasound treatment device, including:

the ultrasonic transducer described above.

In the ultrasonic transducer, the sound emitting surface has the capability of reflecting ultrasonic waves, and the central angle corresponding thereto exceeds 180 degrees, so an ultrasonic wave emitted from part of the sound emitting surface will be reflected back by the opposite part of the sound emitting surface, thereby allowing the ultrasonic wave to be formed as a standing wave in the area, and an ultrasonic wave emitted from other part of the sound emitting surface will not be reflected and is still a traveling wave.

With the combination of the traveling wave and the standing wave, the focal region of the ultrasound can be compressed in some direction(s), so as to change the shape of the focal region from a cigar shape to a regular shape close to a spherical shape, and to reduce the size of the focal region, thereby improving the energy density at the focal region, improving the treatment effect and efficiency, and reducing the damage to normal tissues; meanwhile, scattering, reflection and the like of ultrasound in non-uniform tissues in a human body can be reduced, so as to reduce deviation and distortion of the focal region, thereby facilitating accurate positioning of the focal region.

In addition, the sound emitting surface is provided with three notches, so that a human body, a material to be processed, research equipment and the like can enter the sound emitting surface through the notches and reach the vicinity of the focal region, which facilitates practical application of the ultrasonic transducer.

The ultrasonic transducer of the present disclosure is optionally applied in a focused ultrasound treatment device, and can also be applied in other fields such as scientific research, material processing and the like.

Reference numerals: 1. housing; 2. upper cover; 3. sound emitting surface; 31. first notch; 32. second notch; 33. third notch; 4. piezoelectric array element; 5. end cover; 91. first plane; 92. second plane; 99. main great circle.

DESCRIPTION OF THE INVENTION

In order that those skilled in the art can better understand the technical solutions of the present disclosure, the present disclosure will be further described in detail below with reference to the accompanying drawings and specific implementations.

First Embodiment

As shown in FIGS. 1 to 19, the embodiment provides an ultrasonic transducer including a sound generation unit for generating an ultrasonic wave and a sound emitting surface 3.

Moreover, the sound emitting surface 3 is a spherical surface having a first notch 31, a second notch 32, and a third notch 33. One great circle of a sphere corresponding to the sound emitting surface 3 is a main great circle 99, the first notch 31 and the second notch 32 are respectively located at two intersections of the spherical surface and a diameter perpendicular to the main great circle 99, and the third notch 33 connects the first notch 31 with the second notch 32.

Within certain distances from the main great circle 99 respectively at both sides of the main great circle 99, a cross-section of the sound emitting surface 3 parallel to the main great circle 99 is in the shape of an arc, an opening of the arc corresponds to the third notch 33, and a central angle corresponding to the arc is greater than 180 degrees and less than 360 degrees.

The sound emitting surface 3 has the capability of reflecting ultrasonic waves, and an ultrasonic wave generated by the sound generation unit is focused on the center of the sphere corresponding to the sound emitting surface 3.

The ultrasonic transducer of the embodiment has a sound generation unit, which is a device capable of generating ultrasound. For example, the material of the sound generation unit may include piezoelectric ceramics or 1-3 type piezoelectric composite material. The shape, number, position, and other parameters of the sound generation unit may be designed such that the sound generation unit can emit ultrasound from all positions of the sound emitting surface 3, and the ultrasound emitted at each position propagates along the normal direction of the sound emitting surface 3 at the position, and the ultrasound can be finally focused (including directly focused or focused after being reflected) at a required position.

Figure 1:
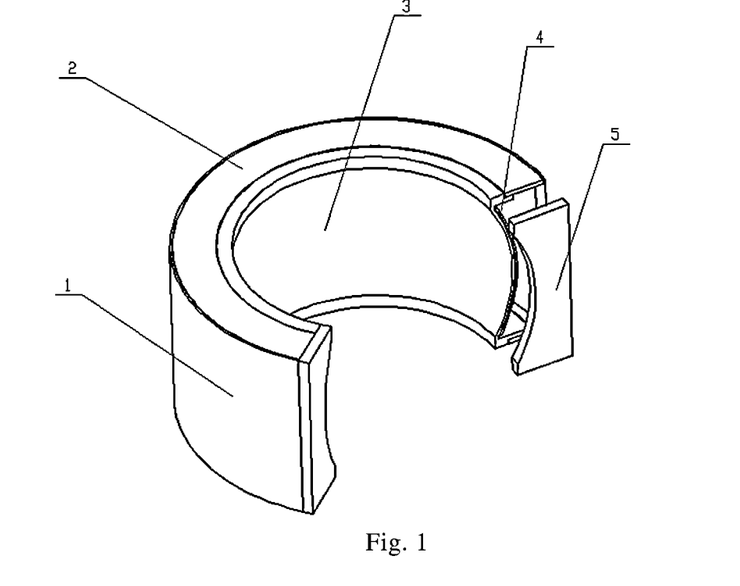
FIG. 1 is a schematic structural diagram of an ultrasonic transducer according to an embodiment of the present disclosure.

Specifically, as shown in FIG. 1, the sound emitting surface 3 may be an acoustically transparent surface with a predetermined shape, and the sound generation unit (e.g., a piezoelectric array element 4) may be disposed behind the sound emitting surface 3; alternatively, the sound emitting surface 3 may be the emitting surface of the sound generation unit itself.

Specifically, the sound generation unit may also take different forms. For example, the sound generation unit may be a plurality of piezoelectric array elements 4 (e.g., rectangular piezoelectric ceramic plates) disposed at different positions of the sound emitting surface 3, that is, the plurality of piezoelectric array elements 4 are spliced together to form the sound emitting surface 3; alternatively, the sound generation unit may also have the same shape as the sound emitting surface 3 (e.g., the sound generation unit is a specially shaped piezoelectric ceramic plate).

Needless to say, as shown in FIG. 1, the ultrasonic transducer may further include, in addition to the sound emitting surface 3 and the sound generation unit, a driving circuit of the sound generation unit, a casing (e.g., the casing of the sound generation unit may include a housing 1, an upper cover 2, a lower cover, an end cover 5, etc.) for enclosing the driving circuit and the sound generation unit, and other components, which will not be described in detail herein.

Unlike the conventional sound emitting surface in the shape of a spherical cap, the sound emitting surface 3 of the ultrasonic transducer of the present embodiment is equivalent to a spherical surface lacking three portions.

Figure 2:
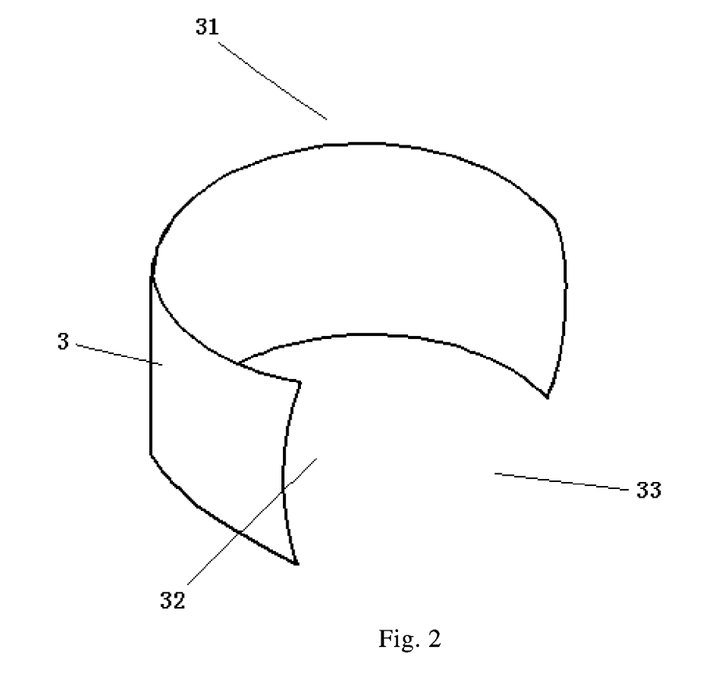
FIG. 2 is a schematic structural diagram of a sound emitting surface in an ultrasonic transducer according to an embodiment of the present disclosure.
Figure 3:
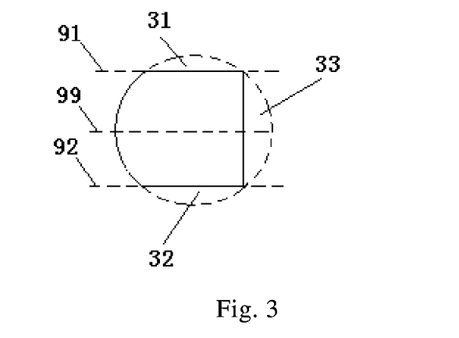
FIG. 3 is a schematic diagram of a structure, in a direction parallel to a main great circle, of a sound emitting surface of an ultrasonic transducer according to an embodiment of the present disclosure.
Figure 4:
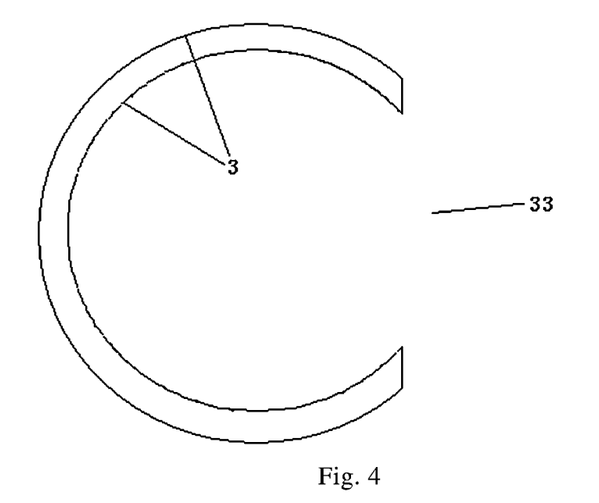
FIG. 4 is a schematic diagram of a structure, in a direction perpendicular to a main great circle, of a sound emitting surface of an ultrasonic transducer according to an embodiment of the present disclosure.

As shown in FIGS. 2 to 4, two portions (the first notch 31 and the second notch 32) missing from the sound emitting surface 3 are portions of the spherical surface at both ends of one diameter, and a great circle (i.e., a plane passing through the spherical center) perpendicular to the diameter is a main great circle 99. The third portion (third notch 33) missing from the sound emitting surface 3 is a portion laterally connecting the first notch 31 with the second notch 32.

That is, if the plane in which the main great circle 99 is located is in a horizontal direction, the diameter perpendicular to the main great circle 99 is in a vertical direction. For a spherical surface, parts of the top end and the bottom end of the spherical surface in the vertical direction may be cut off, respectively, then a part of one side of the spherical surface may be cut off, and the cut-off part of the side should connect the cuts of the top end and the bottom end, so that the remaining spherical surface is the sound emitting surface 3.

Within certain distances (preferably 40 mm to 500 mm, and the distances at two sides may be different) from the main great circle 99 respectively at the two sides of the main great circle 99, a cross-section of the sound emitting surface 3 parallel to the main great circle 99 is an arc, the central angle corresponding to the arc is greater than 180 degrees and less than 360 degrees, and the opening of the arc corresponds to the third notch 33. That is, at least within a certain distance from the main great circle 99, the portion of the spherical surface cut off by the third notch 33 is only a portion less than half sphere, while the remaining sound emitting surface 3 is a portion more than half sphere.

Figure 5:
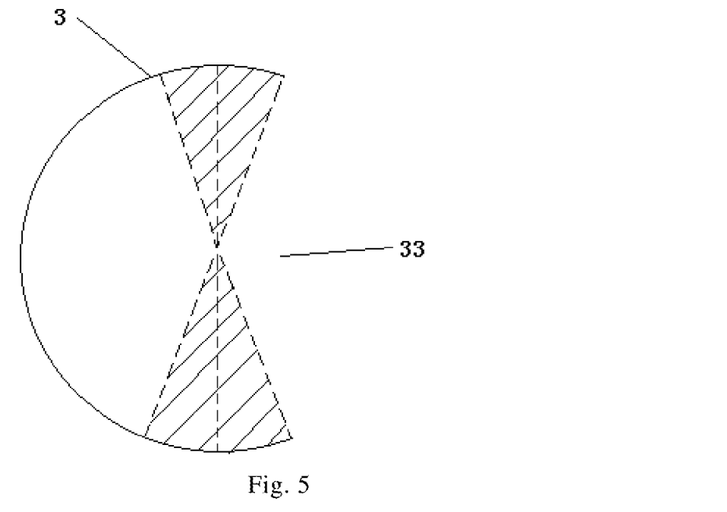
FIG. 5 is a schematic structural diagram of a cross-section of a sound emitting surface parallel to a main great circle in an ultrasonic transducer according to an embodiment of the present disclosure.
Figure 6:
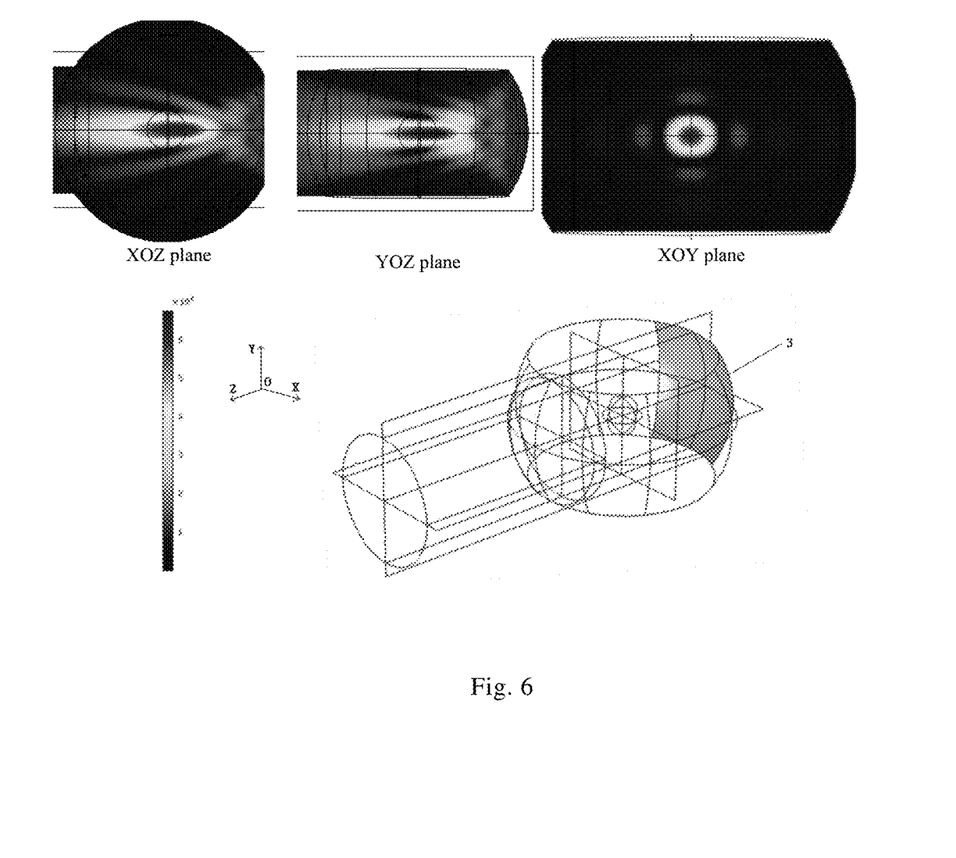
FIG. 6 is a diagram illustrating spatial distribution of simulated acoustic field intensity of a sound emitting surface corresponding to a 60-degree central angle.
Figure 7:
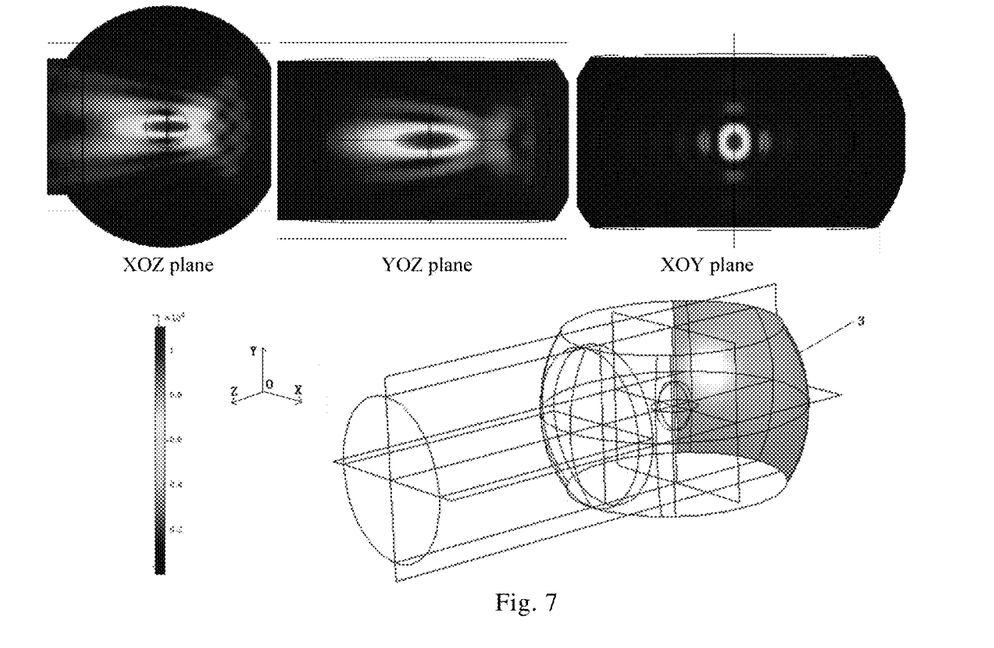
FIG. 7 is a diagram illustrating spatial distribution of simulated acoustic field intensity of a sound emitting surface corresponding to a 100-degree central angle.
Figure 8:
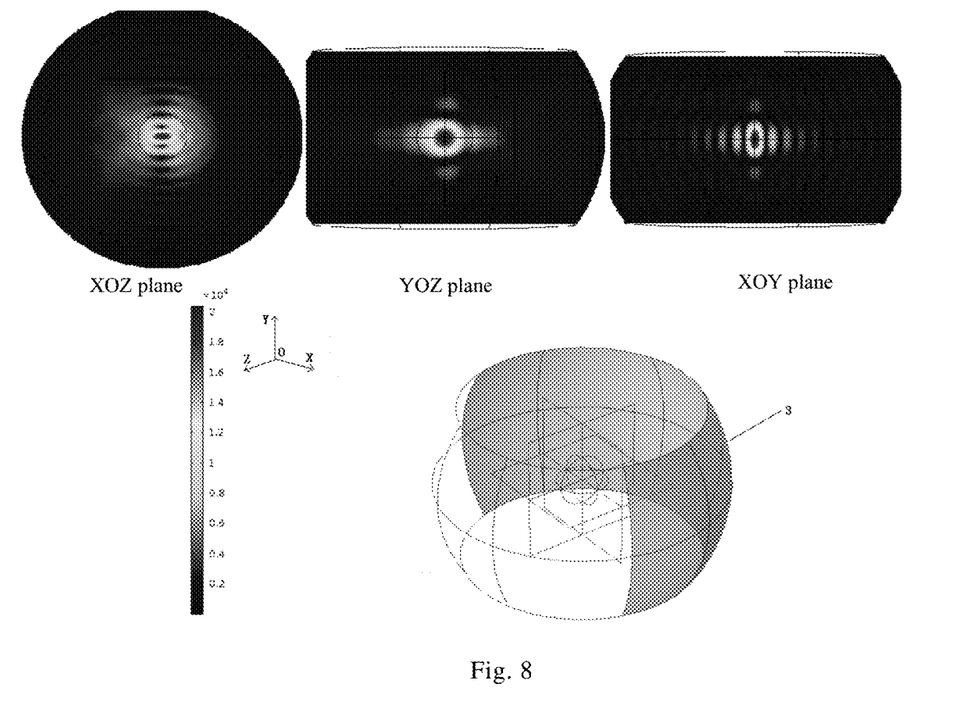
FIG. 8 is a diagram illustrating spatial distribution of simulated acoustic field intensity of a sound emitting surface corresponding to a 220-degree central angle.
Figure 9:
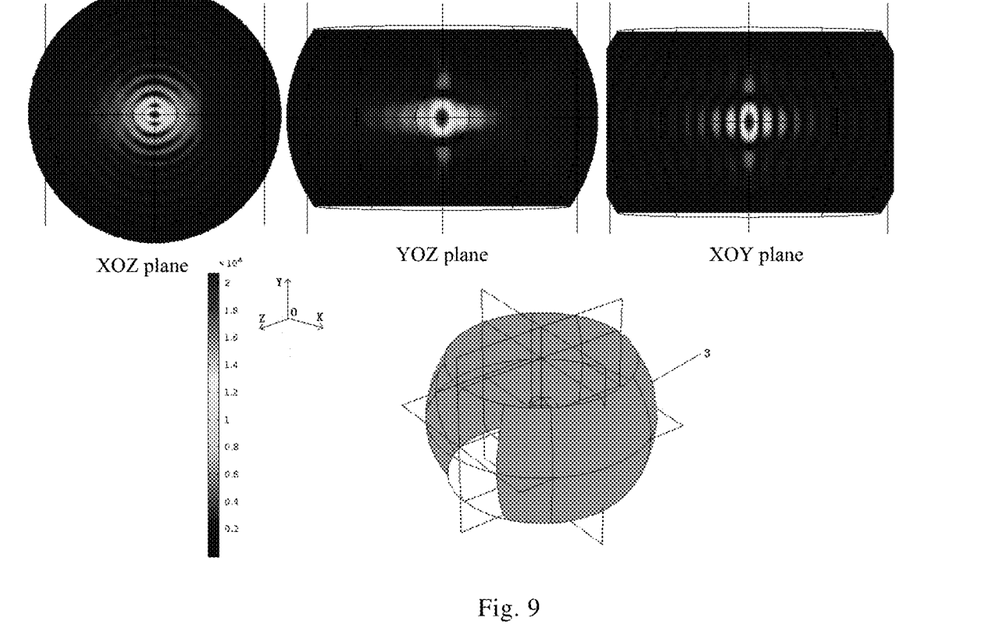
FIG. 9 is a diagram illustrating spatial distribution of simulated acoustic field intensity of a sound emitting surface corresponding to a 300-degree central angle.

Further, since the sound emitting surface 3 has the capability of reflecting ultrasound, as shown in FIG. 5, ultrasound emitted from a part of the arc at an angle exceeding the central angle of 180 degrees is reflected by an opposite part of the sound emitting surface 3, and the part of the arc at the angle exceeding the central angle of 180 degrees may also reflect ultrasound emitted from the opposite part of the sound emitting surface 3, so that ultrasound can return in partial region (the region filled with oblique lines in FIG. 5), so as to form a standing wave, thereby changing the focusing condition and the focal region form of ultrasound; meanwhile, the ultrasound emitted from the part of the arc corresponding to the opening is not reflected, so that ultrasound emitted from this part of the arc is still a traveling wave.

That is, the ultrasound generated by the ultrasound transducer of the embodiment is actually in the form of a combination of a traveling wave and a standing wave, and thus its propagation and focusing will change. Specifically, with the ultrasonic transducer, the major axis of the original cigar-shaped focal region can be compressed, so that the focal region has a shape closer to a spherical shape and has a smaller size, the energy density at the focal region is increased, the treatment effect and efficiency are improved, and damage to normal tissues is reduced. Meanwhile, the ultrasonic transducer can also reduce scattering, reflection and the like of ultrasound in non-uniform tissues in a human body, and reduce deviation and distortion of the focal region, which facilitates accurate positioning of the focal region.

In addition, the sound emitting surface 3 is also provided with three notches, so that a human body, a material to be processed, research equipment and the like can enter the sound emitting surface 3 through the notches and reach the vicinity of the focal region, which facilitates practical application of the ultrasonic transducer.

In an embodiment, edges of the first notch 31 and the second notch 32 are located in a first plane 91 and a second plane 92, respectively. In an embodiment, the first plane 91 and the second plane 92 are both parallel to the main great circle 99.

As shown in FIG. 3, in an embodiment, the first notch 31 and the second notch 32 are spherical caps cut off by planes.

In an embodiment, the first notch 31 and the second notch 32 are spherical caps cut off by two parallel planes, that is, the bottom surfaces of two cut-off spherical caps are parallel to each other. As such, the spherical surface excluding the first notch 31 and the second notch 32 is equivalent to a structure formed by butting the bottom surfaces of two spherical segments. Needless to say, the bottom surfaces of the two spherical segments are the main great circle 99, and the two spherical segments may have different heights. The sound emitting surface 3 has a shape similar to a spherical segment, and is regular and simple in structure.

Needless to say, it is also feasible that the first notch 31 and second notch 32 are cut off by planes that are not parallel to each other, or by curved surfaces that are not planar.

In an embodiment, the distance between the first plane 91 and the second plane 92 ranges from 80 mm to 1000 mm. In an embodiment, the distance between the first plane 91 and the second plane 92 ranges from 150 mm to 500 mm.

That is, the distance between the first notch 31 and the second notch 32 (i.e., the dimension of the sound emitting surface 3 in the vertical direction) is preferably in the above range (of course, the diameter of the sphere corresponding to the sound emitting surface 3 should be larger than the distance), and such sound emitting surface 3 has a sufficient area to generate ultrasound suitable for practical application.

In an embodiment, the distance between the first plane 91 and the main great circle 99 is equal to the distance between the second plane 92 and the main great circle 99.

That is, the first notch 31 and the second notch 32 are preferably obtained by cutting with two planes that have a same distance to the center of the sphere, so that the two notches have a same size and are symmetrically distributed.

Needless to say, it is also possible that the first notch 31 and the second notch 32 have different distances to the center of the sphere, or have different shapes.

In an embodiment, any cross-section of the sound emitting surface 3 parallel to the main great circle 99 is in the shape of an arc, and the central angle corresponding to the arc is greater than 180 degrees and less than 360 degrees.

It is defined above that the sound emitting surface 3 is arc-shaped in a cross-section parallel to the main great circle 99 at least in the vicinity of the main great circle 99. In an embodiment, any cross-section of the sound emitting surface 3 parallel to the main great circle 99 may be in the shape of the arc with a corresponding central angle larger than 180 degrees and smaller than 360 degrees, thereby ensuring that the sound emitting surface 3 can generate a standing wave at each position in the vertical direction.

Needless to say, it is also possible that the sound emitting surface 3 is not in the shape of an arc (e.g., is two separate arcs) at some positions in a cross-section parallel to the main great circle 99.

In an embodiment, the openings of the arcs in any cross-sections of the sound emitting surface 3 parallel to the main great circle 99 face a same direction. In an embodiment, the central angles corresponding to the arcs in any cross-sections of the sound emitting surface 3 parallel to the main great circle 99 are equal.

That is, at different positions in the vertical direction, the third notch 33 is orientated in the same direction, and more preferably has a same corresponding central angle. That is, the third notch 33 is preferably obtained by cutting with a plane perpendicular to the main great circle 99.

As shown in FIG. 4, the sound emitting surface 3 is shaped like the letter "C" as viewed in a direction perpendicular to the main great circle 99, the "C" has a certain thickness in the direction perpendicular to the main great circle 99, and the "C" has different sizes at different positions in the direction perpendicular to the main great circle 99.

In an embodiment, within a certain distance to the main great circle 99 and at each side of the main great circle 99, the central angle corresponding to the arc in the cross-section of the sound emitting surface 3 parallel to the main great circle 99 is more than 180 degrees and less than 300 degrees, preferably more than 200 degrees and less than 280 degrees.

A standing wave can be formed as long as the central angle is more than 180 degrees and less than 360 degrees, but the central angle is more preferably in the above range from the practical point of view. As such, sufficient standing wave can be formed and the third notch 33 is large enough for practical use.

In an embodiment, the sphere corresponding to the sound emitting surface 3 has a diameter in the range of 100 mm to 3000 mm, and more preferably in the range of 200 mm to 2000 mm.

In a case where the shape (the size is not considered) of the sound emitting surface 3 is fixed, the larger the diameter of the corresponding sphere is, the larger the actual size of the sound emitting surface 3 is, so that when the ultrasonic energy emitted per unit area is the same, the larger the total energy of the ultrasonic transducer is, and the higher the energy density of the focal region is. The spherical surface with the above size is more practical.

In an embodiment, the sound emitting surface 3 is symmetrical with respect to the main great circle 99.

As shown in FIG. 3, the sound emitting surface 3 is preferably symmetrical with respect to the main great circle 99, that is, parts of the sound emitting surface 3 respectively on both sides of the main great circle 99 are preferably of the same form, so that the acoustic field and focal region formed by the sound emitting surface are also symmetrical with respect to the main great circle 99, and are more regular and easy to control.

Thereinafter, ultrasound emitted by different sound emitting surfaces 3 is simulated. For each sound emitting surface 3 for simulation, the first plane 91 and the second plane 92 are parallel to each other and have the same distance to the main great circle 99, and cross-sections parallel to the main great circle 99 are in the shape of arcs, and the central angles corresponding to the arcs are the same and face the same direction.

Specifically, spatial distributions of simulated acoustic field intensity (represented by acoustic pressure in Pa) of the sound emitting surfaces 3 respectively having the central angles of 60 degrees, 100 degrees, 220 degrees, and 300 degrees are as shown in FIGS. 6 to 9 (where 0 is the spherical center, Y is the vertical direction, Z is directed to the geometric center of the sound emitting surface 3, and X is perpendicular to both Y and Z, the same applies below).

It can be seen that when the central angle is less than 180 degrees, the focal region is clearly in the shape of an ellipse in the XOZ plane and the YOZ plane, and as the central angle is increased, the major axis of the ellipse is shortened but the change is not significant. This shows that the focal region formed by the existing traveling-wave sound emitting surface 3 is obviously cigar-shaped. When the central angle exceeds 180 degrees, the focal region is in the shape approaching to a circle in the XOZ plane and the YOZ plane, so that the focal region correspondingly has a regular shape close to a sphere. This shows that, when the central angle exceeds 180 degrees, by forming standing waves at partial positions, the dimension of the focal region can be significantly compressed in partial directions, thereby making the focal region approximately spherical.

Figure 10:
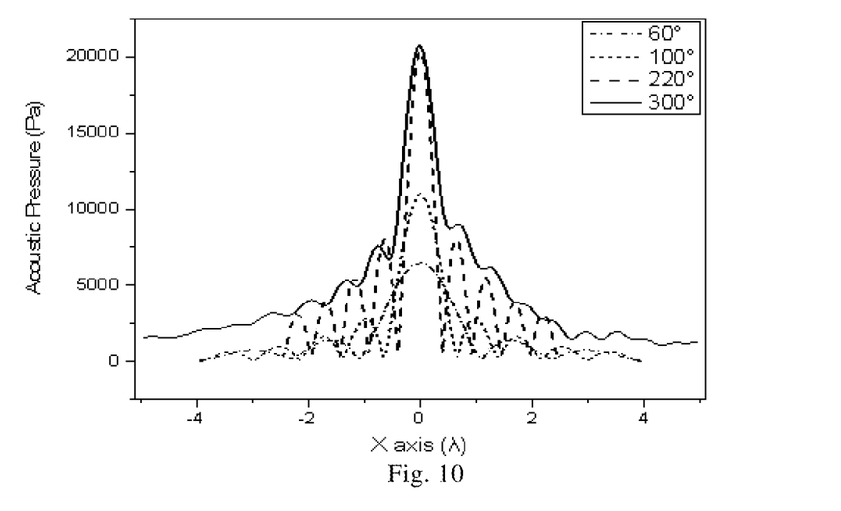
FIG. 10 is a distribution diagram of simulated acoustic field intensity in X-axis of sound emitting surfaces with different central angles.
Figure 11:
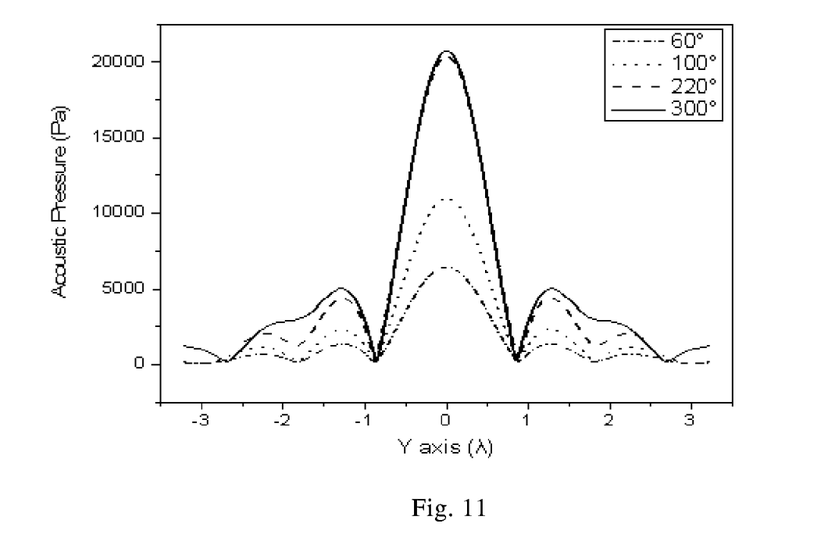
FIG. 11 is a distribution diagram of simulated acoustic field intensity in Y-axis of sound emitting surfaces with different central angles.
Figure 12:
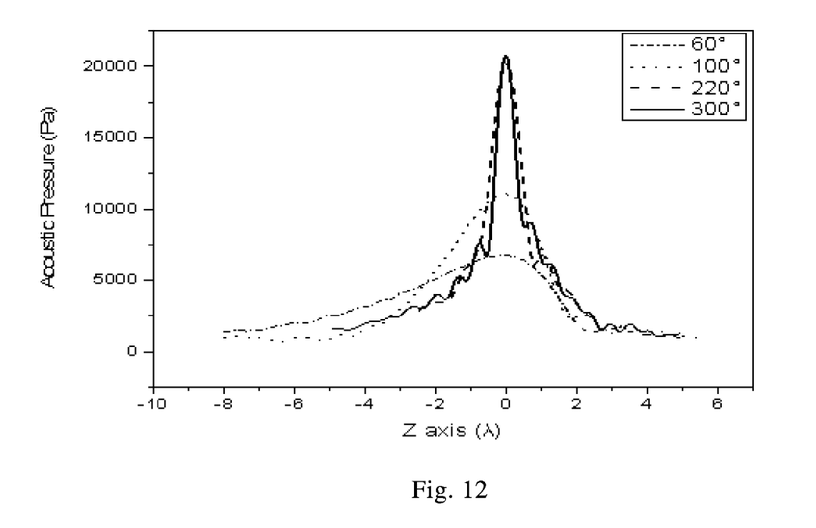
FIG. 12 is a distribution diagram of simulated acoustic field intensity in Z axis of sound emitting surfaces with different central angles.
Figure 13:
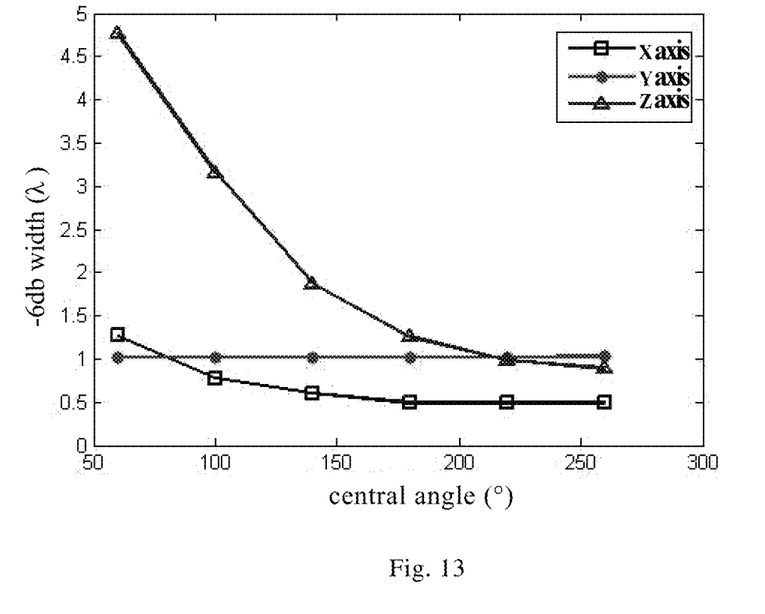
FIG. 13 is a diagram of −6 dB width of simulated acoustic field in each axis of sound emitting surfaces with different central angles.
Figure 14:
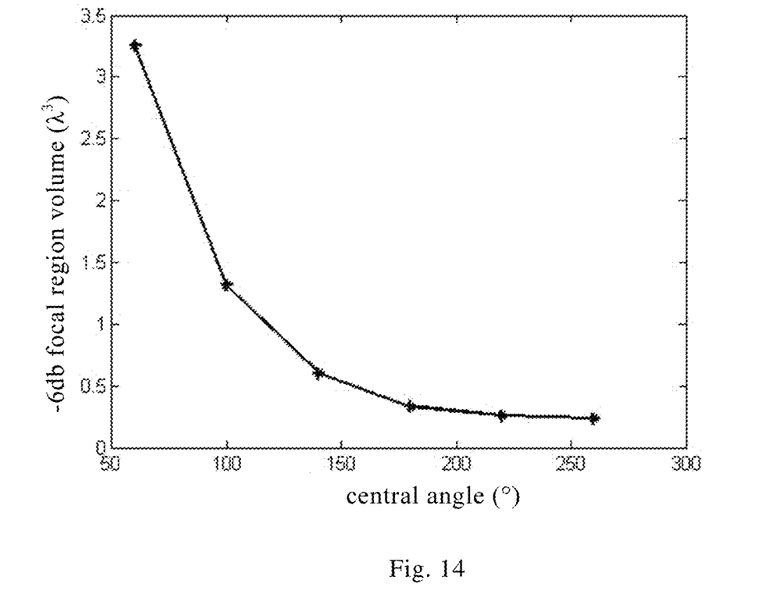
FIG. 14 is a diagram of focal region volume of −6 dB width corresponding to sound emitting surfaces with different central angles.

Further, when the central angles are different, distribution of the simulated acoustic field intensity (represented by acoustic pressure in Pa) in each axis is as shown in FIGS. 10 to 12, −6 dB width of the simulated acoustic field in each axis is as shown in FIG. 13, and the focal region volume of the −6 dB width is as shown in FIG. 14.

As can be seen from the above figures, when the central angle is greater than 180 degrees, the focal region is compressed significantly in the X axis and the Z axis, and especially in the Z axis, the length of the focal region is compressed from nearly 5 wavelengths to approximately 1 wavelength, so that the dimensions of the focal region in the X axis, the Y axis and the Z axis are substantially equal, the focal region changes from a cigar shape to a nearly spherical shape, and the volume is greatly reduced. Meanwhile, as the central angle increases, the maximum value of the acoustic pressure is continuously improved, which shows that the energy density in the focal region is obviously improved along with the reduction of the volume of the focal region.

Figure 15:
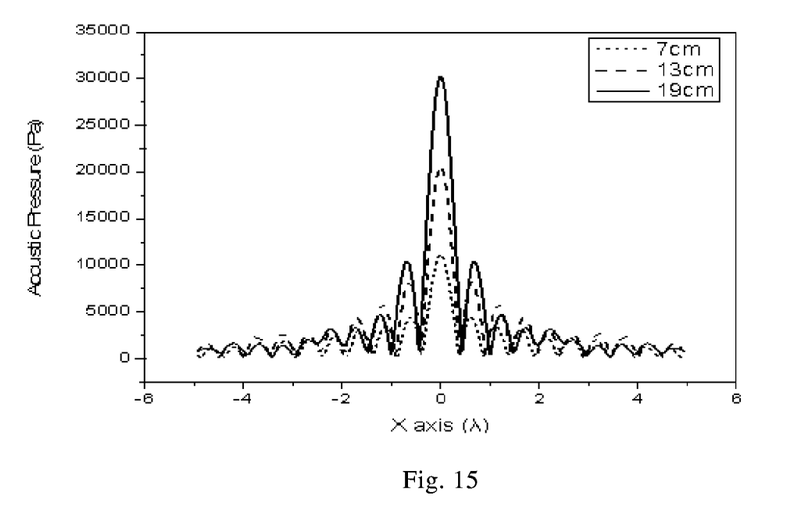
FIG. 15 is a distribution diagram of simulated acoustic field intensity in X-axis of sound emitting surfaces with different dimensions in Y-axis.
Figure 16:
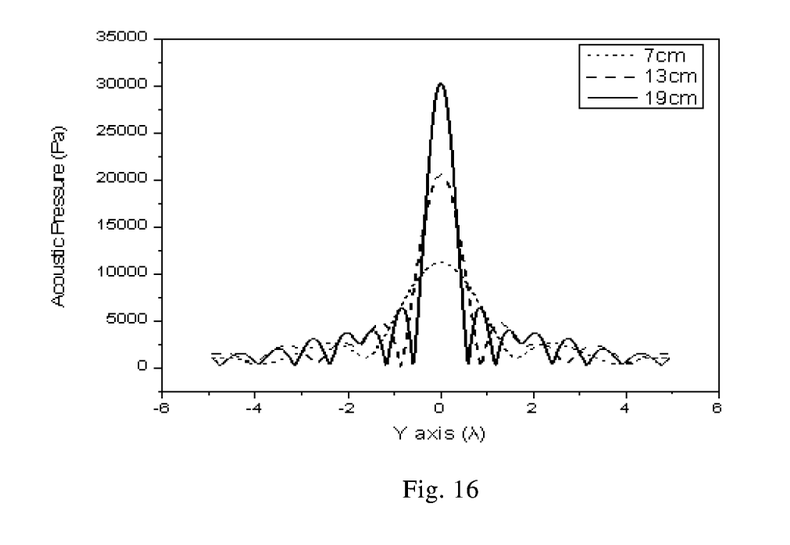
FIG. 16 is a distribution diagram of simulated acoustic field intensity in Y-axis of sound emitting surfaces with different dimensions in Y-axis.
Figure 17:
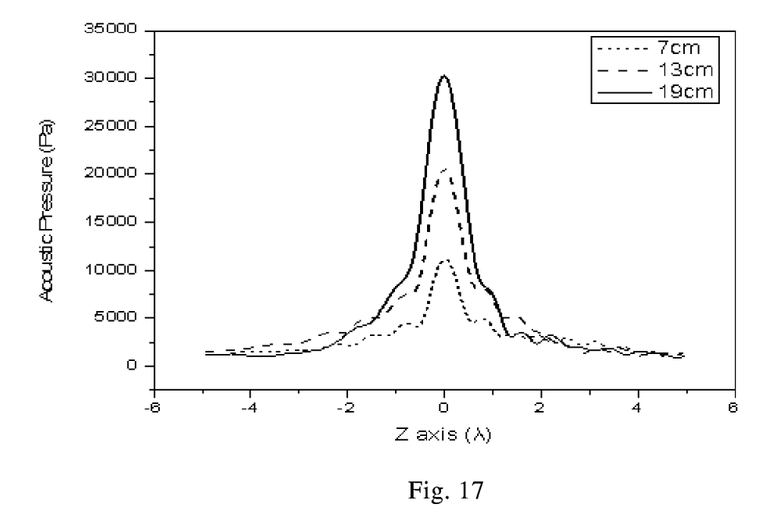
FIG. 17 is a distribution diagram of simulated acoustic field intensity in Z-axis of sound emitting surfaces with different dimensions in Y-axis.
Figure 18:
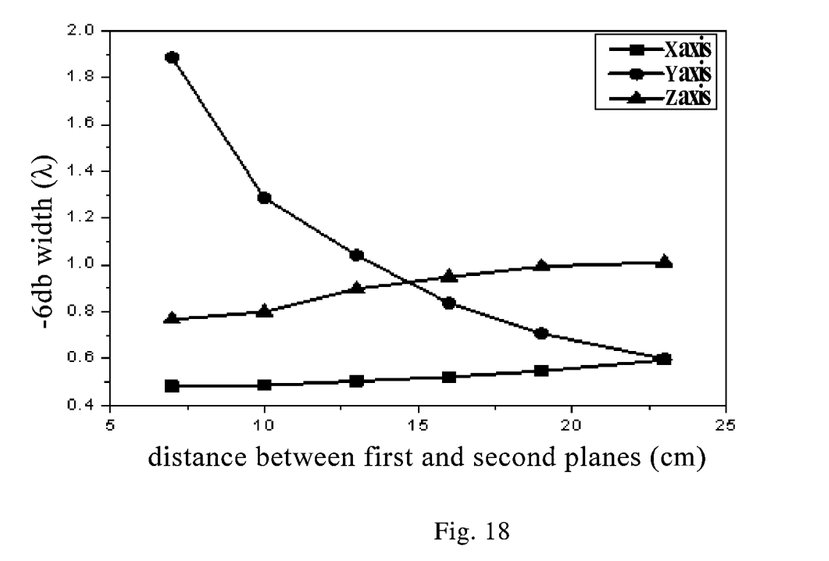
FIG. 18 a diagram of −6 dB width of simulated acoustic field in each axis of sound emitting surfaces with different dimensions in Y-axis.
Figure 19:
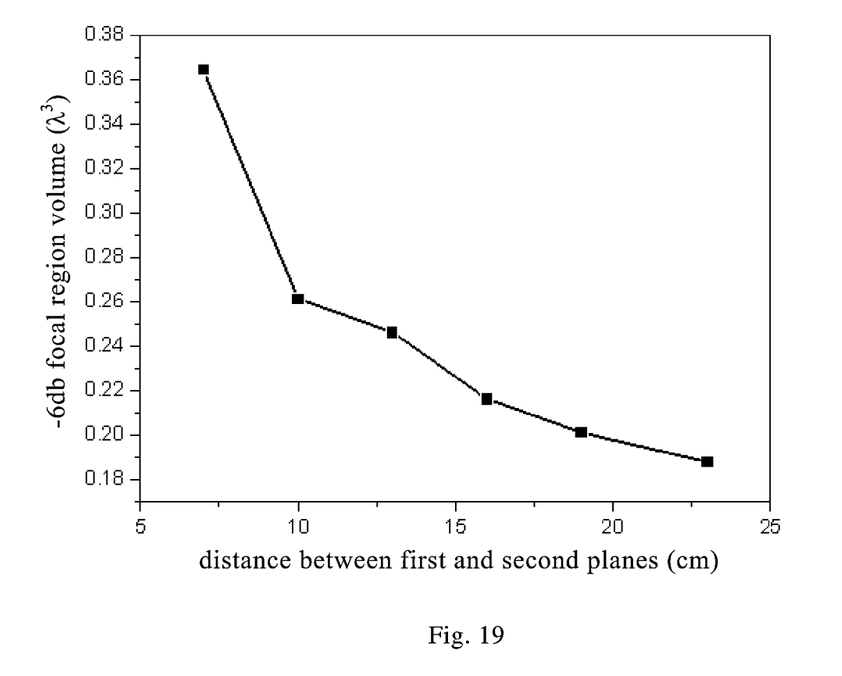
FIG. 19 is a diagram of focal region volume of −6 dB width corresponding to simulated acoustic field of sound emitting surfaces with different dimensions in Y-axis.

When the distance between the first plane 91 and the second plane 92 (i.e., the dimension of the sound emitting surface 3 in the Y-axis direction) changes, distribution of the simulated acoustic field intensity (represented by acoustic pressure in Pa) in each axis is as shown in FIGS. 15 to 17, −6 dB width of the simulated acoustic field in each axis is as shown in FIG. 18, and the focal region volume of the −6 dB width is as shown in FIG. 19.

It can be seen that as the total height (i.e., the dimension of the sound emitting surface 3 in the Y-axis direction) of the spherical segment increases, the size of the focal region is also compressed, and the compression in the Y-axis direction is more significant, and accordingly, the volume of the focal region is significantly reduced. This indicates that the distance between the first plane 91 and the second plane 92 also has an effect on the focal region.

Second Embodiment

The present embodiment provides a focused ultrasound treatment device, which includes: the ultrasonic transducer as described above.

That is, the above-described ultrasonic transducer may be combined with other components to constitute a device for treating diseases using focused ultrasound. For example, the focused ultrasound treatment device may emit ultrasound (e.g., from the outside of a body), and focus the ultrasound at diseased tissues such as liver cancer, breast cancer, kidney cancer, bone tumor, uterine fibroid and the like, so as to treat benign and malignant tumors.

Because the focused ultrasound treatment device of the embodiment adopts the above-described ultrasonic transducer, non-uniform tissues in a human body has small influence on the propagation of ultrasound, and the formed focal region has a regular shape, small size and high energy density. Therefore, the focal region can be accurately positioned at the position of diseased tissue to ablate the diseased tissue quickly, thereby improving the treatment efficiency and effect. Meanwhile, the influence on normal tissues around the diseased tissue and on the beam path can be reduced as much as possible, thereby improving the safety.

Needless to say, according to different treated parts, the shape and size of the ultrasonic transducer in the focused ultrasound treatment device may be different, and the relative position relationship between the sound emitting surface of the ultrasonic transducer and a human body may also be different. For example, the sound emitting surface may be "slipped" on a part of a human body (i.e., the part of the human body passes through the first and second notches) like a "ring"; alternatively, a part of a human body may enter the sound emitting surface through the third notch.

Needless to say, other components may also be included in the focused ultrasound treatment device. For example, a medium containing unit for keeping a sound transmission medium (such as deaerated water) between the sound emitting surface and a surface of a human body may be provided in order to facilitate the entry of ultrasound into the human body. For another example, a treatment couch or the like for supporting the human body may be provided for convenience of treatment. For another example, a driving unit for driving the ultrasonic transducer and/or the human body to move may be further provided to adjust the position of the focal region. For another example, an imaging unit (e.g., type B ultrasound, CT, MRI) for forming an image of an area around the focal region in real time may be provided for evaluating the treatment effect in real time.

It could be understood that the above implementations are merely exemplary implementations for illustrating the principle of the present disclosure, but the present disclosure is not limited thereto. Various modifications and improvements can be made by those skilled in the art without departing from the spirit and essence of the present disclosure, and these modifications and improvements are also considered to be within the protection scope of the present disclosure.

The invention claimed is:

1. An ultrasonic transducer, comprising a sound generation unit and a sound emitting surface, the sound generation unit being configured to generate an ultrasonic wave, wherein
    the sound emitting surface is a spherical surface having a first notch, a second notch and a third notch, wherein one great circle of a sphere corresponding to the sound emitting surface is a main great circle, the first notch and the second notch are respectively positioned at two intersections of the spherical surface and a diameter perpendicular to the main great circle, and the third notch connects the first notch with the second notch;
    within a range of 30 mm to 500 mm from the main great circle respectively at both sides of the main great circle, a cross-section of the sound emitting surface parallel to the main great circle is in a shape of an arc, an opening of the arc corresponds to the third notch, and a central angle corresponding to the arc is larger than 180 degrees and smaller than 360 degrees, the third notch being obtained by cutting with a plane perpendicular to the main great circle;
    the sound emitting surface is capable of reflecting ultrasound, and the ultrasonic wave generated by the sound generation unit is focused on a center of the sphere corresponding to the sound emitting surface; and
    the first notch, the second notch, and the third notch are all capable of allowing a human body or a material to be processed or research equipment to enter the sound emitting surface.

2. The ultrasonic transducer of claim 1, wherein an edge of the first notch and an edge of the second notch are in a first plane and a second plane, respectively.

3. The ultrasonic transducer of claim 2, wherein the first plane and the second plane are both parallel to the main great circle.

4. The ultrasonic transducer of claim 3, wherein a distance between the first plane and the second plane is in a range of 80 mm to 1000 mm.

5. The ultrasonic transducer of claim 4, wherein the distance between the first plane and the second plane is in a range of 150 mm to 500 mm.

6. The ultrasonic transducer of claim 3, wherein a distance between the first plane and the main great circle is equal to a distance between the second plane and the main great circle.

7. A focused ultrasound treatment device, comprising: the ultrasonic transducer of claim 2.

8. The ultrasonic transducer of claim 1, wherein each cross-section of the sound emitting surface parallel to the main great circle is in the shape of the arc, and the central angle corresponding to the arc is larger than 180 degrees and smaller than 360 degrees.

9. The ultrasonic transducer of claim 8, wherein the opening of the arc in each cross-section of the sound emitting surface parallel to the main great circle is oriented in a same direction.

10. The ultrasonic transducer of claim 9, wherein central angles corresponding to the arcs in all cross-sections of the sound emitting surface parallel to the main great circle are equal.

11. A focused ultrasound treatment device, comprising: the ultrasonic transducer of claim 8.

12. The ultrasonic transducer of claim 1, wherein within the certain distances from the main great circle respectively at both sides of the main great circle, the central angle corresponding to the arc in the cross-section of the sound emitting surface parallel to the main great circle is larger than 180 degrees and smaller than 300 degrees.

13. The ultrasonic transducer of claim 12, wherein within the certain distances from the main great circle respectively at both sides of the main great circle, the central angle corresponding to the arc in the cross-section of the sound emitting surface parallel to the main great circle is larger than 200 degrees and smaller than 280 degrees.

14. A focused ultrasound treatment device, comprising: the ultrasonic transducer of claim 12.

15. The ultrasonic transducer of claim 1, wherein a diameter of the sphere corresponding to the sound emitting surface is in a range of 100 mm to 3000 mm.

16. The ultrasonic transducer of claim 15, wherein the diameter of the sphere corresponding to the sound emitting surface is in a range of 200 mm to 2000 mm.

17. A focused ultrasound treatment device, comprising: the ultrasonic transducer of claim 15.

18. The ultrasonic transducer of claim 1, wherein the sound emitting surface is symmetric with respect to the main great circle.

19. A focused ultrasound treatment device, comprising: the ultrasonic transducer of claim 1.

* * * * *